US006627164B1

(12) United States Patent
Wong

(10) Patent No.: US 6,627,164 B1
(45) Date of Patent: Sep. 30, 2003

(54) SODIUM ZIRCONIUM CARBONATE AND ZIRCONIUM BASIC CARBONATE AND METHODS OF MAKING THE SAME

(75) Inventor: Raymond J. Wong, Norman, OK (US)

(73) Assignee: Renal Solutions, Inc., West Lafayette, IN (US)

( * ) Notice: Subject to any disclaimer, the term of this patent is extended or adjusted under 35 U.S.C. 154(b) by 15 days.

(21) Appl. No.: 09/723,396

(22) Filed: Nov. 28, 2000

(51) Int. Cl.$^7$ .............................................. C01G 25/00
(52) U.S. Cl. ......................... 423/71; 423/84; 423/420.2
(58) Field of Search ............................ 423/69, 84, 179, 423/184, 186, 209, 419.1, 420.2, 421, 71

(56) References Cited

U.S. PATENT DOCUMENTS

| | | | |
|---|---|---|---|
| 2,328,381 A | 8/1943 | Jaffe | 285/161 |
| 3,520,298 A | 7/1970 | Lange | 128/213 |
| 3,545,438 A | 12/1970 | De Vires | 128/213 |

(List continued on next page.)

FOREIGN PATENT DOCUMENTS

| | | | |
|---|---|---|---|
| EP | 000152717 A1 | 8/1985 | .................. 604/29 |
| FR | 2 585 251 A1 | 5/1985 | ............ A61M/1/34 |
| FR | 2585251 | 1/1987 | |
| GB | 1 467 880 | 3/1977 | ........... B01D/13/00 |
| JP | 59046964 | 3/1984 | |
| JP | 3-242206 | 10/1991 | |
| JP | 08187284 | 7/1996 | ............ A61M/1/14 |
| SU | 1770285 A1 | 10/1992 | |

OTHER PUBLICATIONS

Pospelova and Zaitsev. "Carbanto–Compounds of Zirconium", Russian Journal of Inorganic Chemistry, vol. 11, #8, Aug. 1966, pp. 995–1004.*
Cobe Renal Care, Inc., "Guide to Custom Dialysis," Product No. 306100–005; Revision E, 9/93, pp. 1–54.
Cobe Renal Care, Inc., "Sorbent Dialysis Primer," Product No. 306100–006; Edition 4, 9/93, pp. 1–51.
"Augmentation of Efficiency by Continuous Flow Sorbent Regeneration Peritoneal Dialysis", A. Gordon et al.. vol. XXII Trans. Amer. Soc. Artif. Int. Organs, 1976, pp. 599–604.
"Centrifugal Artificial Kidney", R. M. Kellogg, IBM Technical Disclosure Bulletin, vol. 14, No. 11, Apr. 1972, pp. 3433–3435.
"Combined Technological–Clinical Approach To Wearable Dialysis", Robert L. Stephen et al., Kidney International, vol. 13, Suppl. 8 (1978), pp. S–125–S–132.
"Development of Continuous Recirculating Peritoneal Dialysis Using a Double Lumen Catheter", Michio Mineshima et al., ASAIO Journal, 1992, pp. M377–M381.
"Important Devices in Biomedical Engineering", John G. Webster, International Biomedical Engineering Days, 1992, pp. 1–9.
"Recirculation Peritoneal Dialysis with Sorbent Redy Cartridge", Rasib M. Raja et al., Nephron 16, (1976), pp. 134–142.

"Recirculating Peritoneal Dialysis with Subcutaneous Catheter", R. L. Stephen et al., American Society For Artificial Internal Organs, vol. XXII, 1976, pp. 575–584.
"Sorbent Based Regenerating Delivery System For Use In Peritoneal Dialysis", A. J. Lewin et al., vol. XX Trans. Amer. Soc. Artif. Int. Organs, 1974, pp. 130–134.
"The Use of Reciprocating Peritoneal Dialysis with a Subcuntaneous Peritoneal Catheter in End–Stage Renal Failure in Diabetes Mellitus", G. D. Warden et al., Journal of Surgical Research, vol. 24, Jun. 1978, pp. 495–500.
"Blood Flow and Pressure Measurement", IBM Technical Disclosure Bulletin, Feb. 1971.
"Continuous Flow Dialyzer", IBM Technical Disclosure Bulletin, Jul. 1975.
"Reciprocating Peritoneal Dialysis", Carl Kablitz, M.D. et al., Dialysis & Transplantation, vol. 7, No. 3, Mar. 1978, pp. 211–212 and 214.
"Reciprocating Peritoneal Dialysis with a Subcuntaneous Peritoneal Catheter", Robert L. Stephen, M.D., Dialysis & Transplantation, vol. 7, No. 8, Aug. 1978.
"Studies on low–cost Disposable Bioreactor for Bilirubin Detoxification", B. Das et al., Proceedings RC IEEE–EMBS & 14$^{th}$ BMESI, 1995, 4.53–4.54.
"Technological Augmentation of Peritoneal Urea Clearance: Past, Present, and Future", Carl Kablitz, M.D. et al., Dialysis & Transplantation, vol. 8, No. 8, Aug. 1960, pp. 741–744 and 778.
E–mail–(1995) D. Halligan, "The Human and Artificial Kidney" from Google Search.
"A Membrane System to Remove Urea from the Dialyzing Fluid of the Artificial Kidney" Kolff, W. J. et al., Annual rept. No. 2, Jul. 1, 1978–Jun. 30, 1979).
"The Regenerative Dialysis (REDY) Sorbent System" Roberts M., Nephrology, 1998, V4, N4 (Aug.), P275–278.
"In search of a 24 Hours Per Day Artificial Kidney" Lande A. J. et al., Journal of dialysis (U.S.) 1977, 1 (8) p. 805–23, ISSN 0362–8558.
"Efficacy of Lumbo–Peritoneal Versus Ventriculo–Peritoneal Shunting for Management of Chronic Hydrocephalus Following Aneurysmal Subarachnoid Haemorrhage" Kang S., Acta Neurochirurgica. 142.
"Performance of the Dialytic Reactor with Product Inhibited Enzyme Reactions: A Model Study" Catapano Gerardo et al., Bioseparation 4 (3):p. 201–211 1994.
Copy of U.S. patent application No. 09/996,505.
Copy of U.S. patent application No. 09/995,888.
International Search Report for PCT/US01/44660.

*Primary Examiner*—Steven Bos
*Assistant Examiner*—Anthony Kuhar
(74) *Attorney, Agent, or Firm*—Kilyk & Bowersox, P.L.L.C.

(57) ABSTRACT

A method of making sodium zirconium carbonate is described which involves forming a mixture of zirconium oxychloride with soda ash and then heating at a sufficient temperature and for a sufficient time to form the sodium zirconium carbonate. Subsequent washing and filtration steps can further form parts of this process. A novel sodium zirconium carbonate is further described which contains from about 2 wt % to about 5 wt % Na$^+$; from about 44 wt % to about 50 wt % ZrO$_2$; from about 12 wt % to about 18 wt % CO$_3^{2-}$; and from about 32 wt % to about 35 wt % H$_2$O.

30 Claims, 1 Drawing Sheet

U.S. PATENT DOCUMENTS

| | | |
|---|---|---|
| 3,669,878 A | 6/1972 | Marantz et al. ................ 210/22 |
| 3,669,880 A | 6/1972 | Marantz et al. ................ 210/22 |
| 3,685,680 A | 8/1972 | Tenckhoff et al. ............. 220/27 |
| 3,697,410 A | 10/1972 | Johnson et al. .............. 204/301 |
| 3,697,418 A | 10/1972 | Johnson ........................ 210/22 |
| 3,703,959 A | 11/1972 | Raymond ..................... 210/87 |
| 3,850,835 A | 11/1974 | Marantz et al. ............. 252/182 |
| 3,888,250 A | 6/1975 | Hill ............................. 128/214 |
| 3,939,069 A | 2/1976 | Granger et al. ................ 210/22 |
| 3,989,622 A | 11/1976 | Marantz et al. ........... 210/22 R |
| 3,989,625 A | 11/1976 | Mason ......................... 210/94 |
| 4,025,608 A | 5/1977 | Tawil et al. ................. 423/305 |
| 4,042,672 A | 8/1977 | Brugger et al. ............. 423/419 |
| 4,088,456 A | 5/1978 | Giorgi et al. .................. 55/179 |
| 4,190,047 A | 2/1980 | Jacobsen et al. ............ 128/213 |
| 4,192,748 A | 3/1980 | Hyden ......................... 210/87 |
| 4,213,859 A | 7/1980 | Smakman et al. ............ 210/27 |
| 4,256,718 A | 3/1981 | McArthur et al. ....... 423/419 P |
| 4,360,507 A | 11/1982 | McArthur et al. ....... 423/419 P |
| 4,412,917 A | 11/1983 | Ahjopalo .................... 210/104 |
| 4,460,555 A | 7/1984 | Thompson .................. 423/309 |
| 4,473,449 A | 9/1984 | Michaels et al. ........... 204/101 |
| 4,474,853 A | 10/1984 | Watanabe ................... 428/403 |
| 4,484,599 A | 11/1984 | Hanover et al. ......... 137/636.1 |
| 4,495,129 A | 1/1985 | Newberry et al. .......... 264/235 |
| 4,521,528 A | 6/1985 | Kovach ...................... 502/208 |
| 4,558,996 A | 12/1985 | Becker ....................... 417/374 |
| 4,560,472 A | 12/1985 | Granzow et al. ........... 210/140 |
| D282,578 S | 2/1986 | Humphreys et al. ......... D24/21 |
| 4,650,587 A | 3/1987 | Polak et al. ................ 210/638 |
| 4,680,122 A | 7/1987 | Barone ...................... 210/637 |
| 4,738,668 A | 4/1988 | Bellotti et al. .............. 604/283 |
| 4,765,907 A | 8/1988 | Scott .......................... 210/648 |
| 5,004,459 A | 4/1991 | Peabody et al. .............. 604/29 |
| 5,032,261 A | 7/1991 | Pyper ........................ 210/137 |
| 5,034,124 A | 7/1991 | Kopf .......................... 210/231 |
| 5,035,805 A | 7/1991 | Freeman et al. ............ 210/689 |
| 5,151,082 A | 9/1992 | Gorsuch et al. ................ 604/4 |
| 5,173,125 A | 12/1992 | Felding ................... 134/22.11 |
| 5,427,683 A | 6/1995 | Gershon et al. ............ 210/264 |
| 5,498,338 A | 3/1996 | Kruger et al. .............. 210/641 |
| 5,520,632 A | 5/1996 | Leveen et al. ................. 604/9 |
| 5,549,674 A | 8/1996 | Humes et al. ................. 623/11 |
| 5,595,909 A | 1/1997 | Hu et al. .................. 435/297.4 |
| 5,597,805 A | 1/1997 | Breborowicz et al. ........ 514/19 |
| 5,631,025 A | 5/1997 | Shockley et al. ........... 424/678 |
| 5,641,405 A | 6/1997 | Keshaviah et al. .......... 210/645 |
| 5,679,231 A | 10/1997 | Alexander et al. .......... 204/627 |
| 5,704,915 A | 1/1998 | Melsky et al. .............. 604/175 |
| 5,712,154 A | 1/1998 | Mullon et al. ........... 435/297.4 |
| 5,782,796 A | 7/1998 | Din et al. ...................... 604/29 |
| 5,824,213 A | 10/1998 | Utterberg .................... 210/241 |
| 5,938,634 A | 8/1999 | Packard ....................... 604/29 |
| 5,944,684 A | 8/1999 | Roberts et al. ................. 604/5 |
| 5,955,450 A | 9/1999 | Breborowicz et al. ........ 514/54 |
| 5,968,966 A | 10/1999 | Bergström .................. 514/400 |
| 5,980,481 A | 11/1999 | Gorsuch ...................... 604/28 |
| 5,984,891 A | 11/1999 | Keilman et al. |
| 6,017,942 A | 1/2000 | Bergström .................. 514/399 |
| 6,074,359 A | 6/2000 | Keshaviah et al. ............ 604/29 |
| 6,117,122 A | 9/2000 | Din et al. .................... 604/408 |
| 6,146,536 A | 11/2000 | Twardowski ................ 210/646 |
| 6,196,992 B1 | 3/2001 | Keilman et al. .............. 604/67 |
| 6,274,103 B1 | 8/2001 | Taylor ........................ 422/261 |
| 6,284,131 B1 | 9/2001 | Hogard et al. .............. 210/143 |
| 6,284,139 B1 | 9/2001 | Piccirillo .................... 210/645 |
| 6,293,921 B1 | 9/2001 | Shinmoto et al. ............. 604/29 |
| 6,299,769 B1 | 10/2001 | Falkvall et al. ............. 210/232 |
| 6,306,836 B1 | 10/2001 | Martis et al. ................. 514/58 |
| 6,309,673 B1 | 10/2001 | Duponchell et al. ........ 424/717 |

* cited by examiner

SODIUM ZIRCONIUM CARBONATE AND ZIRCONIUM BASIC CARBONATE AND METHODS OF MAKING THE SAME

BACKGROUND OF THE INVENTION

The present invention relates to sodium zirconium carbonate, zirconium phosphate, and zirconium basic carbonate and methods of making these compounds.

Sodium Zirconium Carbonate (SZC) is an amorphorous zirconium polymeric compound with the structural formula as shown:

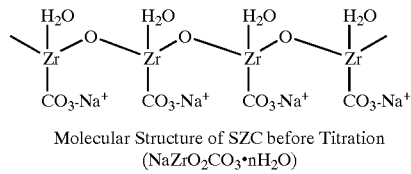

Molecular Structure of SZC before Titration
($NaZrO_2CO_3 \cdot nH_2O$)

The granular form of the material can be obtained by the following two methods:

Method A: Reaction of granular zirconium basic sulfate with a saturated soda ash solution followed by washing the product to remove the sulfate.

Method B: Controlled polymeric particle growth reaction of a metastable sodium zirconium carbonate solution formed by mixing a soluble zirconium salt solution with an excessive amount of soda ash solution.

One industrial application of granular SZC is the conversion of the material to zirconium basic carbonate (ZBC) which is a commercial raw material in making other zirconium chemical products. The conversion can be made by titrating the granular SZC to pH 3.5–4.0 with an acid to remove the excessive sodium carbonate. The granular SZC used for making ZBC is usually produced by Method A. Another important application of SZC is the conversion of the material to the granular zirconium chemical ion exchangers, namely, zirconium phosphate (ZrP) and hydrous zirconium oxide (HZO). These zirconium ion exchange material are used commercially for renal dialysis application. The quality and economic criteria, which dictate the method of their manufacture, constitute the art of making the REDY® sorbent cartridge for hemodialysate regeneration currently used by SORB™ Technology, Inc., Oklahoma City, Okla. A recent study on the design of a sorbent cartridge at SORB™ Technology, Inc. for peritoneal dialysis (PD) fluid regeneration indicates that the granular SZC by itself has unique properties which make it more beneficial than HZO in contributing to the potency of the sorbent PD cartridge. These properties of the material which make the cartridge adaptable to the PD treatment conditions may be summarized as follows:

1. The material has sufficient phosphate adsorption capacity to remove phosphate from the patient fluid for the treatment of hyperphosphatemia in renal disease patients.

2. The material supplements bicarbonate to the PD fluid, which can be essential to correct metabolic acidosis in patients.

3. The material prevents the pH of PD fluid from falling, which may cause depletion of bicarbonate from the patient. This allows regenerative PD to be feasible.

In order to manufacture the granular SZC for sorbent PD applications, both quality and economic factors have to be considered. Method A cannot be used because the product has high sulfate content that degrades the quality of the material as a sorbent. Method B has been used in production through the use of acid zirconium sulfate tetrahydrate (AZST) as the zirconium raw material. The process efficiency is less and the manufacture cost is higher for this process, but the ZrP made from granular SZC has higher ammonium adsorption capacity than that made from zirconium basic sulfate (ZBS).

While these processes are useful, there is a need to provide a better quality sodium zirconium carbonate and zirconium basic carbonate with uses especially in the dialysis area and further there is a need to reduce the cost of manufacturing these components.

SUMMARY OF THE PRESENT INVENTION

The feature of the present invention is to provide an improved sodium zirconium carbonate.

A further feature of the present invention is to provide improved methods to make the sodium zirconium carbonate.

An additional feature of the present invention is to provide a method to make zirconium basic carbonate.

Also, a feature of the present invention is to provide methods to make the zirconium basic carbonate.

Another feature of the present invention is to provide an improved zirconium phosphate and methods to make zirconium phosphates.

An additional feature of the present invention is to provide methods to make the sodium zirconium carbonate, zirconium phosphate, and zirconium basic carbonate more economically and to provide methods which result in a better quality product.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purpose of the present invention, as embodied and broadly described herein, the present invention relates to a method of making sodium zirconium carbonate which involves heating zirconium oxychloride with soda ash at a sufficient temperature and for a sufficient time to form the sodium zirconium carbonate. Preferably, the soda ash is in the form of an aqueous slurry or solution and the zirconium oxychloride is in the form of a powder or solution. Prior to the heating, the zirconium oxychloride and soda ash are preferably agitated or mixed by other means to form a solution mixture at ambient temperatures, such as room temperature. After the heating step, the sodium zirconium carbonate can be washed to remove impurities and any chloride.

The sodium zirconium carbonate, after the initial preparation can be subjected to a titration. Preferably, an alkaline slurry contains the sodium zirconium carbonate and the titration occurs with at least one acidic agent, such as an acid, to obtain a pH below about 7.0. Other additional steps can be used in this process, such as filtering steps, washing steps, and drying steps.

The present invention further relates to a sodium zirconium carbonate which contains from about 2 weight percent to about 5 weight percent $Na^+$;

from about 44 weight percent to about 50 weight percent $ZrO_2$;

from about 12 weight percent to about 18 weight percent $CO_3^{2-}$; and from about 32 weight percent to about 35 weight percent $H_2O$, based on the weight of the sodium zirconium carbonate.

The present invention, in addition, relates to a method of making zirconium basic carbonate which involves titrating an aqueous slurry of a sodium zirconium carbonate to a pH of from about 3.5 to about 4 with an acidic agent. The sodium zirconium carbonate used to form the slurry has a preferred moisture content of from about 15% to about 25% LOD. After titrating, the aqueous slurry is washed with water. The zirconium basic carbonate can then be recovered as a wet powder from the slurry by various techniques.

In addition, the present invention relates to a zirconium basic carbonate characterized by a $Na^+$ content of less than about 1000 ppm;

a $ZrO_2$ wt % of from about 35 wt % to about 40 wt %; and a $CO_3^{2-}$ of from about 8 wt % to about 10 wt % wherein the weight % is based on the composition of the solid powder (final product). Unless stated otherwise, all % and wt %, throughout this application, are wt % based on the weight of the final product.

The present invention further relates to a method of making zirconium phosphate which involves heating zirconium oxychloride with soda ash at a sufficient temperature and for a sufficient time to form sodium zirconium carbonate and treating the sodium zirconium carbonate with caustic soda to form an alkaline hydrous zirconium oxide. Afterwards, the alkaline hydrous zirconium oxide is heated as a slurry, and an acidic agent(s) such as phosphoric acid, is added. After heating, the slurry can be cooled and an acid zirconium phosphate can be filtered off and washed to reduce unreacted leachable phosphate levels. An aqueous slurry can then be formed with the acid zirconium phosphate and this slurry can be titrated with a basic agent, such as caustic soda, until a desired pH is reached, such as a pH of from about 5 to about 6. Afterwards, the titrated product, which is titrated zirconium phosphate, can be filtered and washed to preferably reduce the leachable sodium ions. Then, the zirconium phosphate can be dried to form a free flowing powder preferably having a moisture level of from about 12 to about 18% LOD.

The present invention further relates to a novel zirconium phosphate which preferably has a $Na^+$ content of from about 4 to about 6 wt %; a $ZrO_2$ wt % of from about 34 wt % to about 37 wt %; a $PO_4^-$% of from about 41 wt % to about 43 wt %; and a $H_2O$ wt % of from about 14 wt % to about 18 wt %, based on the weight of the zirconium phosphate. The zirconium phosphate of the present invention preferably has a good adsorption capacity for ammonia, $Ca^{2+}$, $Mg^{2+}$, and toxic heavy metals. Preferably, the zirconium phosphate has no residual sulfate or chloride and satisfies other characteristics desirable in dialysis applications or other ion exchange applications.

It is to be understood that both the foregoing general description and the following detailed description are exemplary and explanatory only and are intended to provide a further explanation of the present invention, as claimed.

The accompanying drawings, which are incorporated in and constitute a part of this application, illustrate embodiments of the present invention and together with the description, serve to explain the principles of the present invention.

DETAILED DESCRIPTION OF THE PRESENT INVENTION

Figure 1:
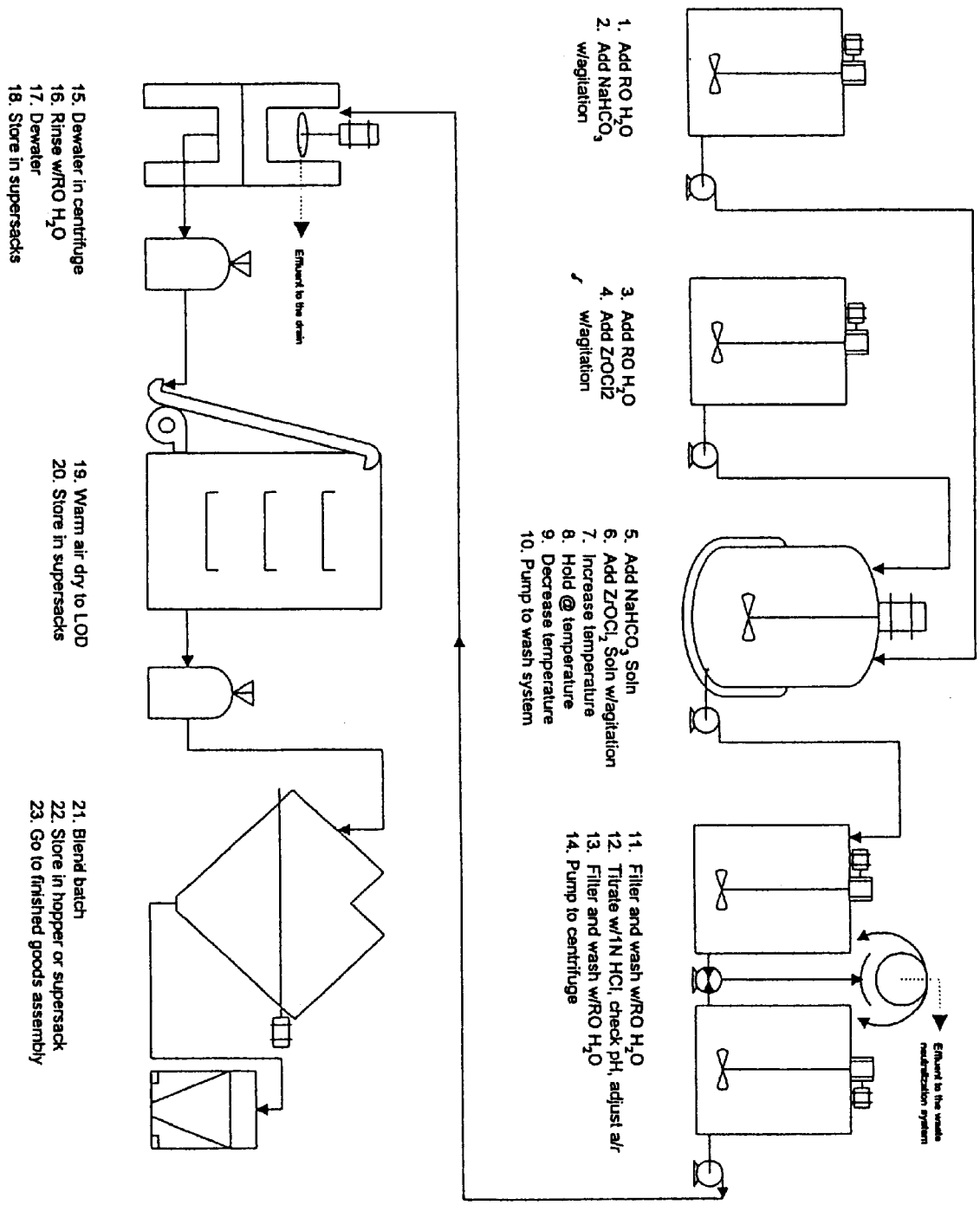
FIG. 1 is a schematic drawing showing one embodiment of preparing sodium zirconium carbonate.

The present invention relates to methods of making sodium zirconium carbonate and to methods of making zirconium basic carbonate and zirconium phosphate. In each instance, the starting materials are preferably zirconium oxychloride. The present invention further relates to novel forms of sodium zirconium carbonate, zirconium phosphate, and zirconium basic carbonate. The sodium zirconium carbonate, the zirconium basic carbonate, and the zirconium phosphate can be used in a variety of industrial applications as raw materials and further can be used in renal dialysis applications and in other separation applications.

In more detail, in an embodiment of the present invention, the present invention relates to a method of making sodium zirconium carbonate. The method involves heating zirconium oxychloride with soda ash at a sufficient temperature and for a sufficient time to form the sodium zirconium carbonate. Prior to heating, the sodium zirconium carbonate may be partially or completely formed.

Preferably, the soda ash is in the form of an aqueous slurry or solution. The amount of the soda ash used to form the solution or slurry is preferably an amount to form a saturated solution or slurry containing soda ash. For instance, from about 260 g to about 920 g of soda ash per liter of water can be used to form the saturated solution or slurry.

The zirconium oxychloride preferably has the formula $ZrOCl_2 \cdot 8H_2O$ and is commercially available from such sources as Teledyne Wah Chang Co., Dastech Int'l, Inc., and Zirconia Sales, Inc. Preferably, the zirconium oxychloride and the soda ash are present in a weight ratio of from about 3.0:1 to about 4.0:1; and more preferably a weight ratio of from about 3.5:1 to about 4.0:1; and even more preferably a weight ratio of about 3.6:1.

The zirconium oxychloride is preferably in the form of a powder or solution. If in a solution, the zirconium oxychloride is preferably present in an amount of about 400 g per liter of water.

With respect to the above process, preferably, prior to the heating step, the zirconium oxychloride and soda ash are agitated or mixed by other means to form a solution mixture preferably at ambient temperature, such as room temperature (e.g., from about 40° F. to about 110° F.). With regard to the metastable sodium zirconium carbonate solution which is achieved prior to the heating step, preferably, a gelatinous precipitate of zirconium carbonate is formed when zirconium oxychloride (solution or solid) is added to soda ash solution. Due to the amphoteric property of the material, the zirconium carbonate re-dissolves in excessive soda ash solution to preferably form a metastable sodium zirconium carbonate (alkaline) solution at room temperature. When the mixing ratio of $ZrOCl_2 \cdot 8H_2O$ to soda ash is optimized and the mixing temperature is preferably maintained in the range of from about 90° to about 95° F. (by the heat of reaction generated during mixing), the material is preferably completely dissolved to form a clear solution. Upon storage at room temperature for a few hours, the solution becomes turbid as precipitate starts to form. The turbidity of the starting solution does not affect the particle size and % recovery of the product. Nevertheless, it is preferred to start heating up the metastable SZC solution at once after it is formed. In the heating step, precipitation of SZC preferably starts to occur at about 150° F. due to saturation. As heating is continued, polymeric SZC particles start to grow to 30–50 micron particle size range at the final temperature (boiling point) of the sodium zirconium carbonate. Preferably, a sufficient temperature is the boiling temperature of the mixture of the zirconium oxychloride and soda ash. For example, the temperature of the heating can be from about 150° F. to about 250° F. (super heating under pressure) for a time of about 2 hours. The equilibration time at the final temperature is about 2 hours. Maximum temperature of heating and long heating time affect the resulting particle size. When heating sodium zirconium carbonate and the soda ash, preferably the heating rate of the mixture is from about 0.5° F. to about 1° F./minute until boiling of the mixture is achieved. The mixture can be heated until the superheating temperature of the mixture is obtained under pressure.

Preferably, the agitation or other mixing means used to obtain the mixture leads to a clear metastable solution at room temperature. During the heating step, preferably, the mixture is slowly agitated or mixed by other means to obtain improved particle growth.

In the above process, and after the heating step, the sodium zirconium carbonate solution can be reduced in temperature from the boiling temperature to about 150° F. or lower. This product solution containing the sodium zirconium carbonate can be filtered off to recover the sodium zirconium carbonate which is preferably in a granular form. Water separation can be achieved by any standard filtering technique, such as using centrifuging or filtration. Afterwards, the filtered sodium zirconium carbonate can be washed with water, such as RO water, to remove any chlorides or other impurities from the sodium zirconium carbonate. Typically, many of these impurities originated from the soda ash.

As a preferred part of the process, an alkaline slurry containing the sodium zirconium carbonate can then be titrated, as an option, with at least one acidic agent to obtain a pH of below about 7 and more preferably a pH of from about 3.5 to about 6.0 and, even more preferably a pH of about 6.0. The acidic agent used for the titration can be any agent capable of reducing the pH of the alkaline slurry and more preferably is an acid and, even more preferably is HCl, such as 1 N HCl. After the titration, the sodium zirconium carbonate can be filtered off as before and optionally washed with, for instance, RO water. This washing step preferably reduces the amount of leachable $Na^+$.

The sodium zirconium carbonate (SZC) recovered from the above-described process with or without the optional steps, but preferably with the optional steps, is generally in the form of a washed sodium zirconium carbonate filter cake. This sodium zirconium carbonate is then preferably dried and is generally dried for a sufficient time to form a free-flowing powder. The drying can occur by any technique, such as putting the filter cake on a tray and drying in an oven. Preferably, the drying temperature is at a temperature range of from about 100° F. to about 150° F. Other temperatures can be used. During the drying of the sodium zirconium carbonate, the moisture content that is eventually achieved is preferably from about 10% LOD to about 60% LOD and more preferably from about 30% LOD to about 35% LOD. FIG. 1 sets forth a preferred process of making the SZC.

The recovered sodium zirconium carbonate preferably has an average particle size of from about 30 microns to about 50 microns, and other particle size ranges can be achieved.

The sodium zirconium carbonate of the present invention preferably, in its final form, has from about 2 wt % to about 5 wt % $Na^+$;

from about 44 wt % to about 50 wt % $ZrO_2$;

from about 12 wt % to about 18 wt % $CO_3^{2-}$; and from about 32 wt % to about 35 wt % $H_2O$, based on the weight of the sodium zirconium carbonate.

The sodium zirconium carbonate of the present invention further preferably satisfies the standards set forth in ANSI/AAMI RD-5-1992 on extractable toxic impurities.

Preferably, the sodium zirconium carbonate of the present invention further achieves one or more of the following properties or characteristics:

a phosphate adsorption having a minimum capacity of from about 30 to about 35 mg $PO_4^-P$/gm SZC;

a minimum $HCO_3^-$ content of from about 2 to about 4 mEq $HCO_3^-$/gm SCZ:

a maximum leachable $Na^+$ content of from about 1.5 to about 2.0 mEq $Na^+$/gm SCZ;

and/or a pH range of the titrated sodium zirconium carbonate of from about 6 to about 7.

Preferably, the sodium zirconium carbonate of the present invention has at least one of the above characteristics and more preferably at least two or three, and even more preferably, all of the above characteristics.

The sodium zirconium carbonate preferably provides the necessary potency requirements for peritoneal dialysis applications by providing a sufficient phosphate adsorption capacity for economic use as a clinical sorbent for the treatment of, for instance, hyperphosphatemia or renal disease patients. Further, the sodium zirconium carbonate of the present invention provides the specified bicarbonate content in a peritoneal dialysis fluid during applications. The present invention further has the minimum leachable Na+ as described above.

In the manufacture of granular SZC, the particle size of the product and % recovery can be important for the process performance especially economics, process efficiency (washing, filtration) and product quality. Bigger particle size may increase the stability of the polymeric particles against attrition loss during washing and improve the filtration efficiency. The stability of the particles during the crystal growth reaction is preferably controlled by the $ZrO_2\%$ of the metastable SZC solution, the ratio of soda ash to $ZrO_2$ in solution, the heating rate of the reaction, the maximum heating temperature, and the heating time. A recovery of 92–98% product in the particle size range 30–40 microns can be achieved by adjusting the process parameters as follows:

TABLE 1

| | |
|---|---|
| $ZrO_2$ % of SZC metastable solution | 5.5–7.0% |
| Reactant ratio of soda ash to $ZrO_2$ in solution | 3.6:1 by weight |
| Heating rate of particle growth reaction | 0.5° F.–1° F./min |
| Maximum heating temperature | Boiling to superheating (under pressure) |
| Continuous heating time at maximum temperature | 2 hours |

The SZC titrated to different pH in the range 3–8 have variant qualities summarized by Table 2. Cartridge performance tests indicate that SZC pH 7–8 may induce phosphate leakage and a spike of Na+ and pH in the initial cartridge effluent when the material is tested in a cartridge for PD application.

TABLE 2

Variant Qualities of Granular SZC
for Dialysis Application as a Function of pH

| SZC pH | Phosphate Adsorption | Leachable Na$^+$ Content | HCO$_3^-$ Content |
|---|---|---|---|
| 3.5 | 35.12 mg PO$_4$—P/gm | — | — |
| 5.0 | — | 0.87 mEq/gm | 2.1 mEq/gm |
| 6.0 | 33.9 mg PO$_4$—P/gm | 1.88 mEq/gm | 3.05 mEq/gm |
| 8.0 | 33.5 mg PO$_4$—P/gm | — | — |

While low pH is favorable for phosphate adsorption and reduction of leachable Na+, it also reduces the bicarbonate content and buffer capacity of the material used for the cartridge. Thus the pH 6.0–6.5 should be the optimum range, as verified by the cartridge performance test. After titration, the material should be washed with plenty of RO water until the Total Dissolved Solid is below 300 ppm level in order to control the leachable Na$^+$ content.

The filter cake after titration and washing should be tray-dried at mild temperature (e.g., 100° F.–150° F.) to the preferred moisture level of from about 30 to about 35% LOD. The final product is preferably not over-dried to prevent the loss of bicarbonate. Drying to different moisture levels can also affect the phosphate adsorption capacity of the material as shown in Table 3. Finally, the dried product should be stored in sealed containers to avoid loss of moisture and bicarbonate content.

TABLE 3

Variation of Phosphate Adsorption Capacity
as a Function of Moisture Level for Granular SZC pH 6.0

| Moisture Level (% LOD) | Phosphate Adsorption Capacity mg PO$_4$—P/gm SZC |
|---|---|
| 10.6% | 21.44 |
| 14.9% | 22.24 |
| 21.0% | 24.0 |
| 28.3% | 27.36 |
| 36.7% | 28.8 |
| 42.9% | 30.16 |
| 51.6% | 29.12 |
| 57.9% | 28.72 |

Cartridge performance tests indicate that granular SZC titrated to pH 6.0 and dried to the moisture level 30–35% LOD has sufficient phosphate adsorption capacity to completely remove the uremic toxin from PD fluid for an 8-hour treatment. The material also has sufficient bicarbonate provision to maintain the pH of the fluid throughout dialysis. The level of spikes of Na$^+$ and pH in the initial cartridge effluent is also tolerable and can be diminished by priming before dialysis.

In addition, the present invention also relates to a method of making zirconium basic carbonate which preferably has the formula:

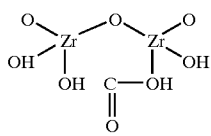

In making the zirconium basic carbonate, an aqueous slurry of sodium zirconium carbonate is titrated to a pH of from about 3.5 to about 4.0 with an acidic agent, such as an acid(s). The sodium zirconium carbonate prior to being introduced into an aqueous slurry preferably has a moisture content of from about 15% to about 25% LOD and more preferably from about 15% to about 20% LOD in solid form. While any sodium zirconium carbonate can be used, preferably the sodium zirconium carbonate formed from the above-described processes is used.

After titration, the aqueous slurry is preferably washed with, for instance, RO water. Afterwards, the zirconium basic carbonate can be recovered as a wet powder from the slurry. The recovery of the zirconium basic carbonate can be achieved by any recovery techniques, such as vacuum filtered or centrifuging or other means. The acidic agent used for titration can be any agent capable of reducing the pH as described above but is more preferably a dilute HCl or HNO$_3$ or other acid or mixtures thereof. Preferably, the final washing of the zirconium basic carbonate is to remove any sodium before any final recovery of the zirconium basic carbonate.

Also, as part of the present invention, the present invention relates to a novel zirconium basic carbonate having Na$^+$ content of less than about 1000 ppm;
 a ZrO$_2$ wt % of from about 35% to about 40%; and
 a CO$_3^{2-}$ wt % of from about 8% to about 10%, based on the weight of the zirconium basic carbonate.

Preferably, the zirconium basic carbonate has essentially no SO$_4^{2-}$ and essentially no Cl$^-$ in the zirconium basic carbonate, e.g., less than about 0.01 wt %.

Again, the zirconium basic carbonate can be used in a variety of industrial applications as well as in sorbent applications.

With respect to the process of making the zirconium phosphate, the process involves similar steps to those used to make the sodium zirconium carbonate. The sodium zirconium carbonate discussed above and achieved after the initial heating step and optional filtering and washing of the sodium zirconium carbonate can be used in this process to form the zirconium phosphate of the present invention. Alternatively, other zirconium oxychlorides can be processed in the manner discussed above to obtain the sodium zirconium carbonate which can then be used through the subsequent steps described below to achieve the desired zirconium phosphate.

In making the zirconium phosphate of the present invention, sodium zirconium carbonate is preferably formed by heating zirconium oxychloride with soda ash at a sufficient temperature and for a sufficient time to form the sodium zirconium carbonate. The starting materials and the temperatures and times that are preferred can be the same as described above with respect to making the sodium zirconium carbonate. The sodium zirconium carbonate formed can then be preferably cooled for instance to a temperature of about 150° F. and optionally subjected to a filtering and washing. Afterwards, the sodium zirconium carbonate can then be treated with a caustic soda or other suitable agent to form alkaline hydrous zirconium oxide. This hydrous zirconium oxide can be in the form of a slurry which is then heated, for instance, in a reactor, at a sufficient temperature and for a sufficient time with an acidic agent, such as phosphoric acid, and more preferably a diluted technical grade phosphoric acid at a 1:1 ratio, with the alkaline hydrous zirconium oxide. Preferably, the heating temperature, as stated above, is at about 180° F. to about 185° F. for about 1 hour. Afterwards, the product can be cooled to a temperature of preferably about 150° F. and filtered off as acid zirconium phosphate (H$^+$ZrP). The acid zirconium phosphate is preferably washed with RO water one or more times to reduce unreacted leachable phosphate levels. Afterwards, an aqueous slurry can be formed with the acid zirconium phosphate and this slurry can be titrated to a pH of about 5 to about 6, and more preferably from about 5.5 to about 6. Preferably, the titrating agent is a 50% caustic soda. Afterwards, the nitrated zirconium phosphate can be filtered and washed to reduce leachable $Na^+$ and more preferably washed with RO water to achieve a 300 ppm or less total dissolved solids to minimize leachable $Na^+$.

Afterwards, the washed zirconium phosphate can be dried to achieve a free flowing powder which preferably has a moisture level of from about 12 to about 18% LOD. Preferably, the drying occurs at a temperature of from about 100° C. to about 120° C. though other temperatures can be used as long as the integrity of the powder is maintained. Preferably, the particle size of the powder is from about 30 microns to about 50 microns, though other sizes can be obtained based on desired parameters.

The washing, filtering, and drying steps mentioned above can be achieved by conventional techniques known to those skilled in the art.

The zirconium phosphate preferably achieved by the process of the present invention has the following characteristics:

$Na^+$ content from about 4 to about 6 wt %

$ZrO_2$ content of from about 34 to about 37 wt %;

$PO_4^-$ content of from about 41 to about 43 wt %; and $H_2O$ content from about 14 to about 18 wt %, based on the weight of the zirconium phosphate.

Furthermore, the zirconium phosphate of the present invention preferably has an adsorption capacity for ammonia, $Ca^{2+}$, $Mg^{2+}$, and toxic heavy metals. More preferably, the adsorption capacity is approximately from about 30 mg $NH_4^-$N/gm ZrP to about 35 mg $NH_4^-$N/gm ZrP, and more preferably about 30 mg $NH_4^-$N/gm ZrP; from about 3 mEq $Ca^{2+}$/gm ZrP to about 5 mEq $Ca^{2+}$/gm ZrP, and more preferably about 3 mEq $Ca^{2+}$/gm ZrP; from about 2 mEq $Mg^{2+}$/gm ZrP to about 3 mEq $Mg^{2+}$/gm ZrP, and more preferably about 2 mEq $Mg^{2+}$/gm ZrP; and from about 5 mEq HM/gm ZrP to about 7 mEq HM/gm ZrP, and more preferably about 6 mEq HM/gm ZrP for heavy metals (HM).

Further, the zirconium phosphate preferably has a $Na^+$ content of from about 2 mEq $Na^+$/gm ZrP to about 3 mEq $Na^+$/gm ZrP, and more preferably about 2.4 mEq $Na^+$/gm and a pH of from about 5.5 to about 6.

Also, the zirconium phosphate of the present invention preferably has a minimum leachable $PO_4^{3-}$ for the material and more preferably is less than about 0.05 mg % $PO_4^{3-}$/gm ZrP.

In addition, the zirconium phosphate preferably has an average grain size of from about 30 to about 40 microns and has no residual sulphate or chloride (e.g., less than 0.01%). Furthermore the zirconium phosphate preferably satisfies the ANSI/AAMI RD-5-1992 standard on extractable toxic impurities and has a pH when in water of from about 6 to about 7. As stated earlier, the zirconium phosphate can be used in a variety of separation devices, such as dialysis separations.

The present invention will be further clarified by the following examples, which are intended to be purely exemplary of the present invention.

EXAMPLES

Example 1

789 gm soda ash was dissolved in 3 liters deionized water. With agitation, 610 gm $ZrOCl_2$ powder was discharged into the soda ash solution. Agitation was continued until the solid was completely dissolved to form a metastable solution. The metastable solution was slowly heated up at the rate 6–10° F. per 10 minutes until the boiling or superheating temperature (under pressure) was reached. The heating was continued at the equilibration temperature for 1.5–2 hours. SZC particles started to form at about 150° F. and continued to grow to 30–50 microns in particle size during the equilibration. Slow agitation was used to obtain better particle growth. The product slurry was then cooled to about 120° F. after heating. The granular SZC was filtered off and the filter cake was washed with deionized water to remove the sodium chloride and excess carbonate. The yield of SZC wet cake was 862 gm and the $ZrO2$% recovery from the metastable solution was found to be 95%.

The SZC wet cake was transferred back to 500 ml deionized water in a beaker. With agitation, the slurry was titrated with 3 N HCl. Equilibration at this pH was continued for 30 minutes and the pH was readjusted to 6.0 afterwards. The titrated SZC was then filtered off and washed with deionized water until the Total Dissolved Solid in the filtrate was less than 300 ppm. The washed filter cake was then dried at mild temperature (about 150° F.) with a tray dryer to about 30% moisture level to form a free-flowing powder.

Example 2

Synthesis of ZrP From Zirconium Oxychloride

The washed filter cake of SZC obtained in Example 1 was transferred to 500 ml of 10% NaOH with agitation. The alkali treatment was continued for half an hour. Then the material was filtered and washed briefly with deionized water. The filter cake was transferred to 1 liter of deionized water in the reactor. The slurry was heated up to about 185° F. 1200 gm of 1:1 diluted phosphoric acid (600 gm 76% $H_3PO_4$ mixed with equal volume of water) was slowly added to the heated slurry until the addition was complete. Heating was then continued at 190°–195° F. for 1 hour. The product slurry was then cooled to 150° F., filtered, and washed with deionized water to remove excessive phosphate. The acid ZrP thus obtained was then titrated to pH 5.75 in 500 ml deionized water with 50% NaOH. The titrated ZrP was then filtered and rinsed with deionized water to remove leachable $Na^+$ until the Total Dissolved Solid in filtrate was less than 300 ppm. The filter cake of titrated ZrP after washing was then dried to 14–18% moisture level with tray dryer to form a free-flowing power.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed is:

1. A method of making a sodium zirconium carbonate free of OH groups comprising heating a mixture of zirconium oxychloride and soda ash at a sufficient temperature and for a sufficient time to form said sodium zirconium carbonate free of OH groups.

2. The method of claim 1, further comprising, prior to said heating, agitating the zirconium oxychloride and soda ash to form a solution mixture at ambient temperature.

3. The method of claim 1, wherein said soda ash is in the form of an aqueous slurry or solution.

4. The method of claim 1, wherein said zirconium oxychloride and soda ash are present in a weight ratio of from about 3.0:1 to about 4.0:1.

5. The method of claim 4, wherein said weight ratio is from about 3.5:1 to about 4.0:1.

6. The method of claim 4, wherein said weight ratio is about 3.6:1.

7. The method of claim 1, wherein said zirconium oxychloride is in the form of a powder or solution.

8. The method of claim 1, wherein said sufficient temperature is the boiling temperature of the mixture of zirconium oxychloride and soda ash.

9. The method of claim 8, wherein the heating occurs for about 2 hours.

10. The method of claim 1, wherein said temperature is from about 150° F. to about 250° F.

11. The method of claim 1, further comprising, after said heating, filtering off the sodium zirconium carbonate.

12. The method of claim 11, further comprising, after filtering, washing any chloride or any impurities from said sodium zirconium carbonate.

13. The method of claim 1, further comprising, after heating, titrating an alkaline slurry comprising said sodium zirconium carbonate with at least one acidic agent to obtain a pH of less than about 7.0.

14. The method of claim 13, wherein said pH is from about 3.5 to about 6.0.

15. The method of claim 13, wherein said pH is about 6.

16. The method of claim 13, further comprising, after titrating, filtering off said sodium zirconium carbonate and washing said sodium zirconium carbonate.

17. The method of claim 16, further comprising, after washing, drying said sodium zirconium carbonate.

18. The method of claim 17, wherein said drying occurs for a sufficient time to form a free flowing powder.

19. The method of claim 17, wherein after said drying, said sodium zirconium carbonate has a moisture content of from about 10% LOD to about 60% LOD.

20. The method of claim 19, wherein said moisture content is from about 30% LOD to about 35% LOD.

21. The method of claim 18, wherein said sodium zirconium carbonate has an average particle size of from about 30 microns to about 50 microns.

22. The method of claim 1, wherein said heating occurs at a heating rate of from about 0.5° F. to about 1° F./minute until boiling temperature of said mixture.

23. A method of making sodium zirconium carbonate comprising mixing zirconium oxychloride with soda ash and agitating to form a solution mixture at ambient temperatures; heating said mixture of zirconium oxychloride and soda ash at a sufficient temperature and for a sufficient time to form said sodium zirconium carbonate, wherein said sufficient temperature is the boiling temperature of the mixture of zirconium oxychloride and soda ash; after said heating, filtering off the sodium zirconium carbonate; after filtering, washing any chloride or any impurities from said sodium zirconium carbonate; titrating an alkaline slurry comprising said sodium zirconium carbonate with at least one acidic agent to obtain a pH of less than about 7.0; after titrating, filtering off said sodium zirconium carbonate and washing said sodium zirconium carbonate; and after washing, drying said sodium zirconium carbonate.

24. A sodium zirconium carbonate comprising from about 2 wt % to about 5 wt % $Na^+$;

from about 44 wt % to about 50 wt % $ZrO_2$;

from about 12 wt % to about 18 wt % $CO_3^{2-}$; and from about 32 wt % to about 35 wt % $H_2O$, based on the weight of the sodium zirconium carbonate.

25. The sodium zirconium carbonate of claim 24, wherein said sodium zirconium carbonate satisfies ANSI/AAMI RD-5-1992 standard on extractable toxic impurities.

26. The sodium zirconium carbonate of claim 24, wherein said sodium zirconium carbonate satisfies at least one of the following characteristics:

a phosphate adsorption having a minimum capacity of from about 30 to about 35 mg/$PO_4$-P/gm SCZ;

a minimum $HCO_3^-$ content of from about 2 to about 4 mEq $HCO_3^-$ gm SCZ;

a leachable $Na^+$ content of from about 1.5 to about 2.0 mEq $Na^+$/gm SCZ;

or a pH range of titrated sodium zirconium carbonate of from about 6 to about 7.

27. The method of claim 1, wherein said zirconium oxychloride and soda ash are mixed at a temperature of from about 40° F. to about 110° F.

28. The method of claim 1, wherein said sodium zirconium carbonate has a formula $NaZrO_2CO_3 \cdot nH_2O$.

29. A method of making a sodium zirconium carbonate comprising:

heating a mixture of zirconium oxychloride and soda ash at a sufficient temperature and for a sufficient time to form said sodium zirconium carbonate; and titrating an alkaline slurry comprising said sodium zirconium carbonate with at least one acidic agent to obtain a pH of less than about 7.0.

30. A method of making a sodium zirconium carbonate comprising:

heating a mixture of zirconium oxychloride and soda ash at a sufficient temperature and for a sufficient time to form said sodium zirconium carbonate, wherein said heating occurs at a heating rate of from about 0.5° F. to about 1° F./minute until boiling temperature of said mixture.

* * * * *